United States Patent
Tran et al.

(10) Patent No.: US 9,068,202 B2
(45) Date of Patent: Jun. 30, 2015

(54) FERMENTATION PROCESS

(75) Inventors: Loan Phuong Tran, Auckland (NZ); Sean Dennis Simpson, Auckland (NZ)

(73) Assignee: LANZATECH NEW ZEALAND LIMITED, Auckland (NZ)

(*) Notice: Subject to any disclaimer, the term of this patent is extended or adjusted under 35 U.S.C. 154(b) by 0 days.

(21) Appl. No.: 13/607,314

(22) Filed: Sep. 7, 2012

(65) Prior Publication Data

US 2013/0065282 A1 Mar. 14, 2013

Related U.S. Application Data

(60) Provisional application No. 61/532,412, filed on Sep. 8, 2011.

(51) Int. Cl.
  *C12P 7/64* (2006.01)
  *C12P 7/06* (2006.01)
  *C12P 7/54* (2006.01)

(52) U.S. Cl.
  CPC .. *C12P 7/06* (2013.01); *Y02E 50/13* (2013.01); *Y02E 50/17* (2013.01); *C12P 7/54* (2013.01); *C12P 7/6463* (2013.01); *C12P 7/649* (2013.01)

(58) Field of Classification Search
  None
  See application file for complete search history.

(56) References Cited

U.S. PATENT DOCUMENTS

| | | |
|---|---|---|
| 5,593,886 A | 1/1997 | Gaddy |
| 5,807,722 A | 9/1998 | Gaddy |
| 5,821,111 A | 10/1998 | Grady et al. |
| 6,136,577 A | 10/2000 | Gaddy |
| 6,340,581 B1 | 1/2002 | Gaddy |
| 6,368,819 B1 | 4/2002 | Gaddy et al. |
| 6,753,170 B2 | 6/2004 | Gaddy et al. |
| 2007/0281349 A1 | 12/2007 | Jaczynski |
| 2010/0159539 A1 | 6/2010 | Ascon et al. |
| 2010/0323417 A1 | 12/2010 | Simpson et al. |
| 2011/0177564 A1 | 7/2011 | Stephanopoulos |

FOREIGN PATENT DOCUMENTS

| | | |
|---|---|---|
| NZ | WO2007/117157 | 10/2007 |
| NZ | WO2008/115080 | 9/2008 |
| WO | WO02/08438 | 1/2002 |
| WO | WO 2008-151149 | 12/2008 |

OTHER PUBLICATIONS

Evans, Christopher T; Ratledge, Colin; "A Comparison of the Oleaginous Yeast, Candida curvata, Grown on Different Carbon Sources in Continuous and Batch Culture" Lipids, 18, 623-629, 1983.*
Balch et al, (1977) International Journal of Systemic Bacteriology., 27:355-361.
Vega et al, (1989) Biotech. Bioeng., 34:785-793.
Klasson et al (1991) Appl. Biochem. Biotech., 24/25: 1.
Demler, M., Weuster-Botz, "Reaction Engineering Analysis of Hydrogenotrophic Production of Acetic Acid by *Acetobacterum woodii*", Biotechnology and Bioengineering, vol. 108, No. 2, Feb. 2011.
Sakai et al, Biotechnology Letters 29: pp. 1607-1612.
Svetlichny, V.A., Sokolova, T.G. et al (1991), Systematic and Applied Microbiology 14: 254-260.
Simpa et. al. Critical Reviews in Biotechnology, 2006 vol. 26. pp. 41-65.
M. Demler and D.Weuster-Botz (2010).
D.R. Martin, A. Misra and H. L. Drake (1985). Dissimilation of Carbon Monoxide to Acetic Acid by Glucose-Limited Cultures of *Clostridium thermoaceticum*. Applied and Environmental Microbiology, vol. 49, No. 6, pp. 1412-1417.
Chi et al.,"Oleaginous yeast Cryptococcus curvatus culture with dark fermentation hydrogen production effluent as feedstock for microbial lipid production" International Journal of Hydrogen Energy, vol. 36, 2011, pp. 9542-9550.

* cited by examiner

*Primary Examiner* — Blaine Lankford
*Assistant Examiner* — David Berke-Schlessel
(74) *Attorney, Agent, or Firm* — Frank S Molinaro (57) ABSTRACT

Methods and systems for the production of one or more lipid products from a gaseous substrate using a two stage fermentation process are provided. The method comprises providing a gaseous substrate comprising $CO_2$ and $H_2$ to a primary bioreactor containing a culture or one or more microorganisms, and fermenting the substrate to produce an acid such as acetate. The acid, e.g. acetate from the primary bioreactor is then provided to a secondary bioreactor, where it is used as a substrate for fermentation to lipids by one or more yeasts.

20 Claims, 2 Drawing Sheets

FERMENTATION PROCESS

CROSS-REFERENCE TO RELATED APPLICATION

This application claims priority of non-provisional application No. 61/532,412 filed on Sep. 8, 2011 which is incorporated by reference in its entirety.

FIELD OF THE INVENTION

This invention relates to a method for the production of lipids from gaseous feedstock. The method comprises a two stage system for the production of one or more lipid products from a gaseous feedstock.

BACKGROUND OF THE INVENTION

The global energy crisis has caused increased interest in alternative approaches to production of fuels. Biofuels for transportation are attractive replacements for gasoline and are rapidly penetrating fuel markets as low concentration blends. Biomass derived biofuel production has emerged as a major approach in increasing alternative energy production and reducing greenhouse gas emissions. The production of biofuels from biomass enables energy independence has been shown to enhance development of rural areas and enhance sustainable economic development.

First generation liquid biofuels utilise carbohydrate feedstocks such as starch, cane sugar, corn, rapeseed, soybean, palm and vegetable oils. The first generation feedstocks present a number of significant challenges. The cost of these carbohydrate feed stocks is influenced by their value as human food or animal feed, while the cultivation of starch or sucrose-producing crops for ethanol production is not economically sustainable in all geographies. The sustained use of these feedstocks as a source for biofuels would inevitably place great strain on arable land and water resources. Therefore, it is of interest to develop technologies to convert lower cost and/or more abundant carbon resources into fuels.

Second generation biofuels are those produced from cellulose and algae. Algae were selected to produce lipids doe to their rapid growth rates and the ability of algae to consume carbon dioxide and produce oxygen.

One area that has seen increased activity is the microbial synthesis of lipids which comprise the raw materials required for bio fuel production. Numerous studies have demonstrated an ability to accumulate lipids through the use of oleaginous yeasts on different substrates such as industrial glycerol, acetic acid, sewage sludge, whey permeate, sugar cane molasses and rice straw hydrolysate. Again these second generation biofuel technologies have encountered problems due to high production costs, and costs associated with the transport and storage of the feedstock.

It has long been recognised that catalytic processes may be used to convert gases consisting of CO, $CO_2$, or hydrogen ($H_2$) into a variety of fuels and chemicals. However, microorganisms may also be used to convert these gases into fuels and chemicals. These biological processes, although generally slower than chemical reactions, have several advantages over catalytic processes, including higher specificity, higher yields, lower energy costs and greater resistance to poisoning.

The production of acetic acid, acetate and other products such as ethanol by the anaerobic fermentation of carbon monoxide, and/or hydrogen and carbon dioxide has been demonstrated. See, e.g., Balch et al, (1977) International Journal of Systemic Bacteriology, 27:355-361; Vega et al, (1989) Biotech. Bioeng., 34:785-793; Klasson et al (1990) Appl. Biochem. Biotech., 24/25: 1; among others.

Acetogenic bacteria, such as those from the genus *Acetobacterium* have been demonstrated to utilize substrates comprising $H_2$, $CO_2$ and/or CO and convert these gaseous substrates into acetic acid, ethanol and other fermentation products by the Wood-Ljungdahl pathway with acetyl co-A synthase being the key enzyme. *Acetobacterium woodii*, a strictly anaerobic, non-spore forming microorganism that grows well at temperatures of about 30° C., has been shown to produce acetate from $H_2$ and $Co_2$. Balch et al. first disclosed the bacterium *A. woodii* which grows by the anaerobic oxidation of hydrogen and reduction of carbon dioxide. Buschorn et al showed the production and utilisation of ethanol by *A. woodii* on glucose. Fermentation of *A. woodii* was performed at glucose (fructose) concentrations of up to 20 mM. Buschorn et al found that when the glucose concentration was increased to 40 mM, almost half of the substrate remained when *A. woodii* entered the stationary growth phase, and ethanol appeared as an additional fermentation product. Balch et al found that the only major product detected by the fermentation of $H_2$ and $CO_2$ by *A. woodii* was acetate according to the following stoichiometry; $4H_2 + 2CO_2 \rightarrow CH_3COOH + H_2O$.

It is an object of the present invention to provide a process and fermentation system that goes at least some way towards overcoming the above disadvantages, or at least to provide the public with a useful choice.

SUMMARY OF THE INVENTION

In a first aspect there is provided a method for producing one or more lipid products from a gaseous substrate, the method comprising;
  i. receiving the gaseous substrate in a first reactor containing a culture of one more microorganisms, and fermenting the gaseous substrate to produce one or more acid(s) and or alcohol(s); and
  ii. passing at least a portion of the one or more acid(s) and or alcohol(s) to a second bioreactor containing a culture of one or more yeasts, and fermenting the one or more acids to produce one or more lipid products.

In one embodiment, the gaseous substrate comprises at least $CO_2$ and $H_2$. In certain embodiments the gaseous substrate is derived from an Industrial source. In certain embodiments one or more gases from one or more industrial sources are blended to provide a gaseous substrate with a desired composition.

In one embodiment the one or more acids is selected from the group consisting of acetate, butyrate, succinate, lactate or propionate.

In one embodiment the one or more alcohols is selected from the group comprising ethanol, butanol, methanol, or propanol.

In various embodiments all of the acid and/or alcohol produced in the first stage is converted to lipids in the second stage. In various embodiments, at least a portion of the acid(s) and or alcohol(s) produced in the first stage is recovered.

In a second aspect there is provided a method for producing one or more lipid products from a gaseous substrate comprising $CO_2$ and $H_2$, the method comprising;
  i. receiving the gaseous substrate in a primary bioreactor containing a culture of one more microorganisms, and fermenting the gaseous substrate to produce one or more acid(s); and ii. passing at least a portion of the one or more acid(s) to a secondary bioreactor containing a culture of one or more yeasts, and fermenting the one or more acids to produce one or more lipid products.

In one embodiment the one or more acid(s) is acetate and the one or more microorganisms is selected from the group consisting of *Acetobacterium woodii* and *Moorella thermoaceticum*.

In one embodiment of the invention, the pH of the fermentation in the primary bioreactor is maintained between around pH 6 to around pH 8. In a preferred embodiment the pH is maintained at pH 7.

In one embodiment the lipids produced by the second stage are used to produce one or more tertiary products. In one embodiment the one or more tertiary products are selected from the group comprising ethanol and biodiesel.

In a third aspect there is provided a method for producing one or more products by anaerobic microbial fermentation, the method comprising;
  i. receiving a substrate comprising $CO_2$ and $H_2$ into a first primary bioreactor containing a culture of one or more microorganisms selected from the group consisting of *Acetobacterium, Moorella, Clostridium, Ruminococcus, Acetobacterium, Eubacterium, Butyribacterium, Oxobacter, Methanosarcina, Methanosarcina*, and *Desulfotomaculum*; and anaerobically fermenting the substrate from step to produce a fermentation broth comprising acetate
  ii. feeding the fermentation broth into a secondary bioreactor containing a culture of one or more yeasts; and
  iii. fermenting acetate to produce one or more lipids products.

In one embodiment the combined fermentation broth is processed to remove at least a portion the acetate prior to the stream being fed to the secondary bioreactor.

It would be understood that the following embodiments can be applied to any one of the aspects described above.

In one embodiment the pH of the combined fermentation stream is adjusted to be between pH6 and pH8 prior to being fed to the secondary bioreactor.

In one embodiment of the invention the ratio of acetic acid to nitrogen in the fermentation broth in the secondary bioreactor is at least 10:1. In one embodiment the ratio of carbon to acetic acid in the fermentation broth of the secondary bioreactor is 49:1. In one embodiment of the invention, the acid stream exiting the first bioreactor is treated to provide a purified or concentrated acid stream to be passed to the second bioreactor. In one embodiment of the invention carbon:nitrogen ratio of the fermentation broth in the second bioreactor is monitored, and the input of carbon and nitrogen to the bioreactor is adjusted to ensure a carbon:nitrogen ratio of greater than 49:1

In one embodiment if the invention the acetate produced in the primary bioreactor has a concentration of at least about 5 g/L or at least about 10 g/L, or at least about 15 g/L or at least about 20 g/L.

In one embodiment of the invention the production rate of acetate in the primary bioreactor is at least about 20 g/L/day or at least about 40 g/L/day or at least about 60 g/L/day.

In one embodiment of the invention, the one or more yeasts is oleaginous yeast. In one embodiment of the invention the oleaginous yeast is selected from the group comprising *Candida, Lipomyces, Rhodosporidium, Rhodotorula, Saccharomyces* and *Yarrowia*. In a preferred embodiment the one or more yeasts is *Cryptococcus curvatii*.

In one embodiment of the invention the pH of the fermentation in the secondary bioreactor is maintained at between around pH 6 to around pH 8. In a preferred embodiment the pH is maintained at pH 7.

In one embodiment of the invention the pH in the secondary bioreactor is substantially the same as the pH in the primary bioreactor. In alternative embodiments, the pH of the stream exiting the primary bioreactor is adjusted to about pH 7 prior to being fed to the secondary bioreactor.

In one embodiment of the invention the lipid concentration in the second bioreactor is at least about at least 10 g/L or at least about 20 g/L, or at least about 40 g/L, or at least about 60 g/L, or at least about 80 g/L, or at least about 100 g/L, or at least about 150 g/L In one embodiment of the invention, the lipid production rate in the second bioreactor is at least about 5 g/L/day, or at least about 7 g/L/day, or at least about 10 g/L/day, or about 15/g/L/day, or at least about 20 g/L/day, or at least about 30 g/L/day.

In one embodiment of the invention, the method is a continuous two stage fermentation. In one embodiment, the method is a semi continuous two stage fermentation.

In one embodiment all of the acetate produced in the primary bioreactor is transferred to the secondary bioreactor for fermentation to lipids.

In one embodiment, at least a portion of the acetate produced in the primary bioreactor is recovered.

In one embodiment, at least a portion of the stream exiting the secondary bioreactor is recycled to a primary reactor. In one embodiment, the exit stream is processed to remove substantially all of the biomass prior to being passed to the primary reactor. In certain embodiments the exit stream is further treated to remove soluble proteins and other unwanted components. In other embodiments the pH of the stream is adjusted prior to being fed into the primary reactor.

In one embodiment the lipids produced in the secondary bioreactor are used to produce one or more tertiary products. In one embodiment the one or more tertiary products are selected from the group comprising ethanol, biodiesel, fatty acid methyl esters (FAME) and fatty acid ethyl esters (FAEE).

In one embodiment a series of primary rectors are used to feed at least one secondary reactor. For example three primary reactors to feed one secondary reactor, four primary reactors feeding two secondary reactors etc.

In one embodiment the gaseous substrate is a waste or off gas from an industrial process. In one embodiment the waste gas is selected from the group comprising tail gas from a hydrogen plant, coke oven gas, natural gas, catalytic reformer gas, naphtha cracker offgas, refinery fuel gas, methanol plant tail gases, ammonia plant tail gases, and lime kiln gases.

The invention may also includes the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

BRIEF DESCRIPTION OF THE DRAWINGS

The invention will now be described in more detail and with reference to the accompanying figures, in which.

DETAILED DESCRIPTION OF THE INVENTION

The present invention generally relates to a process of producing alcohols by fermentation of gaseous substrates containing $CO_2$. The methods of the present invention also generally relate to improvements in carbon capture, wherein $CO_2$ is converted into useful products, namely alcohols.

DEFINITIONS

Unless otherwise defined, the following terms as used throughout this specification are defined as follows:

Permeate—substantially soluble constituents of the broth that pass through the separator and are not retained by the separator. The permeate will typically contain soluble fermentation products, by-products and nutrient solution.

Dilution rate—the rate of replacement of the broth in a bioreactor. The dilution rate is measured in the number of bioreactor volumes of broth that are replaced by nutrient medium per day.

Fermentation broth or broth—the mixture of components (including the broth culture and nutrient medium) found in the bioreactor.

Nutrient medium—the solution added to the fermentation broth containing nutrients and other components appropriate for the growth of the microorganism culture.

Substrate comprising carbon monoxide—and like terms should be understood to include any substrate in which carbon monoxide is available to one or more strains of bacteria for growth and/or fermentation, for example.

Broth bleed—the portion of the fermentation broth removed from a bioreactor that is not passed to a separator.

Broth culture—the microorganism culture present in the fermentation broth.

Broth culture density—the density of microorganism cells in the fermentation broth.

Separator—a module that is adapted to receive fermentation broth from a bioreactor and pass the broth through a filter to yield a retentate and a permeate. The filter may be a membrane, e.g. cross-flow membrane or a hollow fibre membrane.

Gaseous substrate comprising carbon dioxide and hydrogen—and like terms includes any gas which includes carbon dioxide and hydrogen. Carbon dioxide and hydrogen can be present in varying proportions i.e. substantially same % of both, or more hydrogen, or more carbon dioxide.

Acid—as used herein this term includes both carboxylic acids and the associated carboxylate anion, such as the mixture of free acetic acid and acetate present in a fermentation broth as described herein. The ratio of molecular acid to carboxylate in the fermentation broth is dependent upon the pH of the system. The term "acetate" includes both acetate salt alone and a mixture of molecular or free acetic acid and acetate salt, such as the mixture of acetate salt and free acetic acid present in a fermentation broth as may be described herein. The ratio of molecular acetic acid to acetate in the fermentation broth is dependent upon the pH of the system.

Lipids as used herein include fatty acids, glycolipids, shpingolipids, saccharolipids, polyketides, sterol lipids and prenol lipids.

Bioreactor or fermenter—includes a fermentation device consisting of one or more vessels and/or towers or piping arrangements, which includes the Continuous Stirred Tank Reactor (CSTR), Immobilized Cell Reactor (ICR), Trickle Bed Reactor (TBR), Moving Bed Biofilm Reactor (MBBR), Bubble Column, Gas Lift Fermenter, Membrane Reactor such as Hollow Fibre Membrane Bioreactor (HFMBR), Static Mixer, or other vessel or other device suitable for gas-liquid contact.

Primary bioreactor—as used herein this term is intended to encompass one or more reactors that may be connected in series of parallel with a secondary bioreactor. The primary bioreactors use anaerobic fermentation to produce acids from a gaseous substrate. At least a portion of the acid product of the one or more primary bioreactors is used as a substrate in one or more secondary bioreactor(s).

Secondary bioreactor—as used herein these terms are intended to encompass any number of further bioreactors that may be connected in series or in parallel with the primary bioreactors. Any one or more of these further bioreactors may also be connected to a further separator.

Fermenting, fermentation process or fermentation reaction—and like terms as used herein, are intended to encompass both the growth phase and product biosynthesis phase of the process. As is described further herein, in some embodiments the bioreactor may comprise a first growth reactor and a second fermentation reactor. As such, the addition of metals or compositions to a fermentation reaction should be understood to include addition to either or both of these reactors.

Processes of producing acids by anaerobic fermentation of gaseous substrates are known in the art.

While the following description focuses on certain embodiments of the invention, it should be appreciated that the invention may be applicable to production of other alcohols and or acids and the use of other substrates as will be known by persons of ordinary skill in the art to which the invention relates upon consideration of the present disclosure. Also, while particular mention is made to fermentation carried out using *Acetobacterium woodii* and *Moorella thermoaceticum* the invention is also applicable to other microorganisms which may be used in the same or different processes which may be used to produce useful products, including but not limited to alcohols such as ethanol.

As defined above, in one aspect, the invention relates to processes of producing lipid products from gaseous substrates using a two stage fermentation process. In a first stage a gaseous substrate comprising $CO_2$ and $H_2$ is anaerobically fermented to produce one or more acids. In second stage of the process, the one or more acids from the first stage is fed to a second bioreactor containing a culture of one or more yeasts. The one or more acid(s) is aerobically fermented to produce one or more lipid products.

The process of one aspect of the invention comprises, culturing, in a primary bioreactor containing a liquid nutrient medium, one or more strains of anaerobic, acetogenic bacteria that are capable of producing acetate a from a $CO_2$ and $H_2$ containing substrate, and supplying said gaseous substrate to the bioreactor. The fermentation process produces acetate. The acetate produced in the primary bioreactor is fed to a secondary bioreactor containing a culture of one or more oleaginous yeasts, capable of producing lipid(s) from an acetate containing substrate.

The one or more strains of anaerobic acetogenic bacteria capable of producing acetate from a $CO_2$ and $H_2$ containing substrate are from the group consisting of *Acetobacterium, Moorella, Clostridium, Pyrococcus, Eubacterium, Desulfobacterium, Cabroxydothermus, Acetogenium, Acetoanaerobium, Butyribaceterium, Peptostreptococcus, Ruminococcus, Oxobacter* and *Methanosarcina*. More particularly the bacterium is selected from the group consisting of *Acetobacterium woodii* and *Moorella thermoaceticum*.

The efficiency of the fermentation processes of the various aspects of the invention can be further improved by a further process of recycling a stream exiting the secondary bioreactor to at least one primary reactor. The stream exiting the secondary bioreactor may contain unused metals, salts and other nutrient components. By recycling the exit stream to a primary reactor, the cost of providing a continuous nutrient media to the primary reactor can be reduced. This recycling step has the further benefit or reducing the water requirements of the continuous fermentation process. The stream exiting the bioreactor can be treated before being passed back to a primary reactor. In preferred embodiments, the biomass is separated and processed to recover one or more lipid products. The substantially biomass free stream can then passed to a primary reactor. Alternatively the biomass free stream can be further treated to remove soluble proteins or other unwanted components prior to being passed to the primary reactor. Additional metals and salts can be added to the stream returning to the primary reactor to provide a nutrient stream having a desired composition. The pH of the stream is monitored and adjusted according the fermentation process occurring in the primary reactor.

Fermentation Utilising a Carbon Dioxide and Hydrogen Substrate.

The invention has particular applicability to supporting the production of acetate and ethanol from gaseous substrates such as $CO_2$ and $H_2$ containing industrial flue gases. One such type of gas stream is tailgas from hydrogen production plants, which typically contains 50-60% $CO_2$, 20-30% $H_2$, 5-15% CO, and 5-15% $CH_4$. Another industrial process resulting in a $CO_2$ and $H_2$ rich tail gas is ammonia manufacture. Similar streams are produced from processing of any carbon based feedstock, such as petroleum, coal, and biomass. The invention is also applicable to reactions which produce alternative alcohols.

Processes for the production of ethanol and other alcohols from gaseous substrates are known. Exemplary processes include those described for example in WO2007/117157, WO2008/115080, U.S. Pat. No. 6,340,581, U.S. Pat. No. 6,136,577, U.S. Pat. No. 5,593,886, U.S. Pat. No. 5,807,722 and U.S. Pat. No. 5,821,111, each of which is incorporated herein by reference.

A number of anaerobic bacteria are known to be capable of carrying out the fermentation of $CO_2$ and $H_2$ to alcohols, including ethanol, and acetic acid, and are suitable for use in the process of the present invention. Acetogens have the ability to convert gaseous substrates such as $H_2$, $CO_2$ and CO into products including acetic acid, ethanol and other fermentation products by the Wood-Ljungdahl pathway. Examples of such bacteria that are suitable for use in the invention include those of the genus *Acetobacterium*, such as strains of *Acetobacterium woodii* ((Demler, M., Weuster-Botz, "Reaction Engineering Analysis of Hydrogenotrophic Production of Acetic Acid by *Acetobacterum Woodii*", Biotechnology and Bioengineering, Vol. 108, No. 2, February 2011) and.

*Acetobacterium woodii* has been shown to produce acetate by fermentation of gaseous substrates comprising $CO_2$ and $H_2$. Buschhorn et al. demonstrated the ability of *A. woodii* to produce ethanol in a glucose fermentation with a phosphate limitation.

Other suitable bacteria include those of the genus *Moorella*, including *Moorella* sp HUC22-1, (Sakai et al, Biotechnology Letters 29: pp 1607-1612), and those of the genus Carboxydothermus (Svetlichny, V. A., Sokolova, T. G. et al (1991), Systematic and Applied Microbiology 14: 254-260).

Further examples include *Morella thermoacetica*, *Moorella thermoautotrophica*, *Ruminococcus productus*, *Acetobacterium woodii*, *Eubacterium limosum*, *Butyribacterium methylotrophicum*, *Oxobacter pfennigii*, *Methanosarcina barkeri*, *Methanosarcina acetivorans*, *Desulfotomaculum kuznetsovii* (Simpa et. al. Critical Reviews in Biotechnology, 2006 Vol. 26. Pp41-65). In addition, it should be understood that other acetogenic anaerobic bacteria may be applicable to the present invention as would be understood by a person of skill in the art. It will also be appreciated that the invention may be applied to a mixed culture of two or more bacteria.

One exemplary micro-organism suitable for use in the present invention is *Acetobacterium woodii* having the identifying characteristics of the strain deposited at the German Resource Centre for Biological Material (DSMZ) under the identifying deposit number DSM 1030.

Culturing of the bacteria used in a method of the invention may be conducted using any number of processes known in the art for culturing and fermenting substrates using anaerobic bacteria. Exemplary techniques are provided in the "Examples" section below. By way of further example, those processes generally described in the following articles using gaseous substrates for fermentation may be utilised: M. Demler and D. Weuster-Botz (2010). Reaction Engineering Analysis of Hydrogenotrophic Production of Acetic Acid by *Acetobacterium woodii*. Biotechnology and Bioengineering 2010; D. R. Martin, A. Misra and H. L. Drake (1985). Dissimilation of Carbon Monoxide to Acetic Acid by Glucose-Limited Cultures of *Clostridium thermoaceticum*. Applied and Environmental Microbiology, Vol 49, No. 6, pages 1412-1417. Typically, fermentation is carried out in any suitable bioreactor, such as a continuous stirred tank reactor (CTSR), a bubble column reactor (BCR) or a trickle bed reactor (TBR). Also, in some embodiments of the invention, the bioreactor may comprise a first, growth reactor in which the micro-organisms are cultured, and a second, fermentation reactor, to which fermentation broth from the growth reactor is fed and in which most of the fermentation product (ethanol and acetate) is produced.

The $CO_2$ and $H_2$ Containing Substrate

Preferably the carbon source for the fermentation can be a gaseous substrate comprising carbon dioxide in combination with hydrogen. Similarly, the gaseous substrate may be a $CO_2$ and $H_2$ containing waste gas obtained as a by-product of an industrial process, or from some other source. The largest source of $CO_2$ emissions globally is from the combustion of fossil fuels such as coal, oil and gas in power plants, industrial facilities and other sources.

The gaseous substrate may be a $CO_2$ and $H_2$-containing waste gas obtained as a by-product of an industrial process, or from some another source such as from automobile exhaust fumes. In certain embodiments, the industrial process is selected from the group consisting of hydrogen manufacture, ammonia manufacture, combustion of fuels, gasification of coal, and the production of limestone and cement. The gaseous substrate may be the result of blending one or more gaseous substrates to provide a blended stream. It would be understood to a skilled person that waste gas streams rich in $H_2$ or rich in $CO_2$ are more abundant that waste gas streams rich in both $H_2$ and $CO_2$. A skilled person would understand that blending one or more gas streams comprising one of the desired components of $CO_2$ and $H_2$ would fall within the scope of the present invention.

Hydrogen rich gas streams are produced by a variety of processes including steam reformation of hydrocarbons, and in particular steam reformation of natural gas. The partial oxidation of coal or hydrocarbons is also a source of hydrogen rich gas. Other sources of hydrogen rich gas include the electrolysis of water, by-products from electrolytic cells used to produce chlorine and from various refinery and chemical streams.

Gas streams typically rich in Carbon dioxide include exhaust gasses from combustion of a hydrocarbon, such as natural gas or oil. Carbon dioxide is also produced as a by-product from the production of ammonia, lime or phosphate and from natural carbon dioxide wells.

Blending of Streams

As noted previously, it may be desirable to blend an industrial waste stream with one or more further streams in order to improve efficiency, acid and/or alcohol production and/or overall carbon capture of the fermentation reaction.

Accordingly, where industrial streams have a high $CO_2$ content, but include minimal or no $H_2$, it may be desirable to blend one or more streams comprising $H_2$ with the waste stream comprising $CO_2$, prior to providing the blended substrate stream to the fermenter. The overall efficiency, alcohol productivity and/or overall carbon capture of the fermentation will be dependent on the stoichiometry of the $CO_2$ and $H_2$ in the blended stream. However, in particular embodiments the blended stream may substantially comprise $CO_2$ and $H_2$ in the following molar ratios: at least 1:2 at least 1:4 or at least 1:6 or at least 1:8 or at least 1:10.

Blending of streams may also have further advantages, particularly in instances where a waste stream comprising $CO_2$ and or $H_2$ is intermittent in nature. For example, an intermittent waste stream comprising $CO_2$ and or $H_2$ may be blended with a substantially continuous stream comprising $CO_2$ and or $H_2$ and provided to the fermenter. In particular embodiments of the invention, the composition and flow rate of the substantially continuous stream may be varied in accordance with the intermittent stream in order to maintain provision of a substrate stream of substantially continuous composition and flow rate to the fermenter.

Blending of two or more streams to achieve a desirable composition may involve varying flow rates of all streams, or one or more of the streams may be maintained constant while other stream(s) are varied in order to 'trim' or optimise the substrate stream to the desired composition. For streams that are processed continuously, little or no further treatment (such as buffering) may be necessary and the stream can be provided to the fermenter directly. However, it may be necessary to provide buffer storage for streams where one or more is available intermittently, and/or where streams are available continuously, but are used and/or produced at variable rates.

Those skilled in the art will appreciate it will be necessary to monitor the composition and flow rates of the streams prior to blending. Control of the composition of the blended stream can be achieved by varying the proportions of the constituent streams to achieve a target or desirable composition. For example, a base load gas stream may be predominantly $CO_2$, and a secondary gas stream comprising a high concentration of $H_2$ may be blended to achieve a specified $H_2:CO_2$ ratio. The composition and flow rate of the blended stream can be monitored by any means known in the art. The flow rate of the blended stream can be controlled independently of the blending operation; however the rates at which the individual constituent streams can be drawn must be controlled within limits. For example, a stream produced intermittently, drawn continuously from buffer storage, must be drawn at a rate such that buffer storage capacity is neither depleted nor filled to capacity.

At the point of blending, the individual constituent gases will enter a mixing chamber, which will typically be a small vessel, or a section of pipe. In such cases, the vessel or pipe may be provided with static mixing devices, such as baffles, arranged to promote turbulence and rapid homogenisation of the individual components.

Buffer storage of the blended stream can also be provided if necessary, in order to maintain provision of a substantially continuous substrate stream to the bioreactor.

A processor adapted to monitor the composition and flow rates of the constituent streams and control the blending of the streams in appropriate proportions, to achieve the required or desirable blend may optionally be incorporated into the system. For example, particular components may be provided in an as required or an as available manner in order to optimise the efficiency of alcohol productivity and/or overall carbon capture.

In certain embodiments of the invention, the system is adapted to continuously monitor the flow rates and compositions of at least two streams and combine them to produce a single blended substrate stream of optimal composition, and means for passing the optimised substrate stream to the fermenter.

By way of non limiting example, particular embodiments of the invention involve the utilisation of carbon dioxide gas from lime or cement production as a source of $CO_2$. Typically, such streams contain little or no $H_2$, therefore it may be desirable to combine the stream comprising $CO_2$ with a stream comprising $H_2$ in order to achieve a more desirable $CO_2:H_2$ ratio. $H_2$ is often produced in large quantities at a steel mill in the coke oven. Accordingly, a waste stream from the coke oven comprising $H_2$ can be blended with a lime kiln waste stream comprising $CO_2$ to achieve a desirable composition.

Other sources of $CO_2$ and/or $H_2$ that may be blended to form a $CO_2/H_2$ substrate stream include ammonia and urea synthesis.

The gaseous substrate may also be a $CO_2$ and $H_2$-containing waste gas obtained from some other source such as from automobile exhaust fumes. In these embodiments, the $CO_2$ and $H_2$ containing gas may be captured from the industrial process before it is emitted into the atmosphere, using any convenient method. Depending on the composition of the gaseous $CO_2$ and $H_2$ containing substrate, it may also be desirable to treat it to remove any undesired impurities, such as dust particles before introducing it to the fermentation. For example, the gaseous substrate may be filtered or scrubbed using known methods.

The $CO_2$ and $H_2$ containing substrate may also be sourced from fermentation processes wherein carbohydrates or gases are fermented to form products such as ethanol. For example, the anaerobic fermentation of a gaseous substrate comprising CO by microorganisms from the genus *Clostridium* results in the production of products including ethanol. $CO_2$ and optionally hydrogen are by-products of the fermentation reaction.

In some embodiments of the invention, the substrate comprising $CO_2$ is derived from carbon containing waste, for example, industrial waste gases or from the gasification of other wastes. As such, the methods of the invention represent effective processes for capturing carbon that would otherwise be exhausted into the environment. In certain embodiments, the methods provide improved processes for capturing $CO_2$ by conversion into useful products such as acids and/or alcohols.

The $CO_2$ and $H_2$ containing substrate will typically contain a major proportion of $H_2$, such as at least about 30% $H_2$ by volume, or at least 40% $H_2$ by volume, or at least 50% $H_2$ by volume, or at least 60% H$_2$ by volume, or at least 70% H$_2$ by volume, or at least 80% H$_2$ by volume, or at least 85% H$_2$ by volume.

The gaseous substrate will typically contain at least about 10% CO$_2$ by volume, or at least 15% CO$_2$ by volume, or at least 20% CO$_2$ by volume, or at least 25% CO$_2$ by volume, or at least 30% CO$_2$ by volume, or at least 40% CO$_2$ by volume.

Methods for Separating CO$_2$ from other gaseous components are well known. Separation technologies can be sorted into three general categories; post-combustion, pre-combustion and oxyfuel. Post combustion technologies use solvents to absorb CO$_2$ from the flue gas after combustion. Pre-combustion technologies separate CO$_2$ from the feed fuel, using well known processes such as hydrocarbon gasification and water-shift reaction, and uses the remaining hydrogen gas as fuel. Oxyfuel plants replace air with pure oxygen in the combustion chamber. When burned with pure oxygen, hydro carbons emit an almost pure stream of CO$_2$ and steam, facilitating end separation of CO$_2$.

It would be understood by a skilled person that, a hydrocarbon stream can be passed through a number of processes in order to produce the substrate comprising CO$_2$ and H$_2$. For example, in accordance with one aspect of the invention a hydrocarbon stream (CH$_4$) passes through a Steam Methane Reformer to produce a gas stream comprising at least CO and H$_2$; the gas stream then undergoes a Water Gas Shift reaction to produce a substrate comprising CO, CO$_2$ and H$_2$. The substrate can be passed through a Pressure Swing Adsorber (PSA) to separate at least a portion of gases. IT would be understood that more than one PSA stage can be used to enable separation of different components of the gas stream.

As the skilled addressee would understand, the CO$_2$ component of the substrate and the H$_2$ component of the gas steam can be derived from separate sources. The CO$_2$ component can be derived from an industrial waste gas stream typically rich in carbon dioxide, and hydrogen from an alternative source can be blended with the CO$_2$ to produce a CO$_2$ and H$_2$ substrate having the desired composition. Known separation techniques can be used to separate out the desired components of each industrial waste gas, and the desired components can be blended together to form the substrate comprising CO$_2$ and H$_2$.

Typically the carbon dioxide will be added to the fermentation reaction in a gaseous state. However, the methods of the invention are not limited to the addition of carbon dioxide in this state. Carbon dioxide is readily dissolvable in water. At room temperature, the solubility of CO$_2$ is about 90 cm$^3$ of CO$_2$ per 100 ml of water. Carbon dioxide exists in many forms in aqueous solution. When added to an aqueous solution CO$_2$ dissolves.

Equilibrium between the dissolved CO$_2$ and hydrogen carbonate is then established;

Hydrogen carbonate then dissociates;

The amount of the various forms of carbon dioxide present in aqueous solution is dependent on the factors including pH of the solution, as well as pressure and temperature conditions. The presence of other ions in solution can also affect the amount of the different forms of carbon dioxide present in solution.

A skilled person would understand that Carbon dioxide could be provided to the fermentation in aqueous form. A skilled person would also understand that it would be possible to provide CO$_2$ to the fermentation reaction in both gaseous and aqueous forms.

Reaction Stoichiometry

Anaerobic bacteria have been demonstrated to produce ethanol and acetic acid from CO, CO$_2$ and H$_2$ via the Acetyl-CoA biochemical pathway.

The stoichiometry for the formation of acetate from a substrate comprising H$_2$ and CO$_2$ by acetogenic bacterial including *Acetobacterium woodii* is as follows (Balch et al., 1977):

For growth of the bacteria and CO$_2$ and H$_2$-to-acid and/or alcohol fermentation to occur, in addition to the CO$_2$ and H$_2$-containing substrate gas, a suitable liquid nutrient medium will need to be fed to the bioreactor. A nutrient medium will contain vitamins and minerals sufficient to permit growth of the micro-organism used. Anaerobic media suitable for the fermentation of acetate and/or ethanol using CO$_2$ as the sole carbon source are known in the art. For example, suitable media are described in U.S. Pat. Nos. 5,807,722 and 6,340,581. The present invention provides a novel media which has increased efficacy in supporting growth of the micro-organisms and/or alcohol production in the fermentation process. This media will be described in more detail hereinafter.

The fermentation should desirably be carried out under appropriate conditions for the CO$_2$ and H$_2$-to-acetate and/or ethanol fermentation to occur. Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO$_2$ in the liquid phase does not become limiting, and maximum product concentrations to avoid product inhibition. Suitable conditions are described in WO02/08438, WO07/117,157 and WO08/115,080.

The optimum reaction conditions will depend partly on the particular micro-organism used. However, in general, it is preferred that the fermentation be performed at pressure higher than ambient pressure. Operating at increased pressures allows a significant increase in the rate of CO$_2$ transfer from the gas phase to the liquid phase where it can be taken up by the micro-organism as a carbon source for the production of ethanol. This in turn means that the retention time (defined as the liquid volume in the bioreactor divided by the input gas flow rate) can be reduced when bioreactors are maintained at elevated pressure rather than atmospheric pressure.

It is also desirable that the rate of introduction of the CO$_2$ and H$_2$ containing gaseous substrate is such as to ensure that the concentration of CO$_2$ and H$_2$ in the liquid phase does not become limiting. This is because a consequence of CO$_2$ and H$_2$-limited conditions may be that the ethanol product is consumed by the culture.

The optimum temperature for fastest growth of the bacteria, and highest production rate of acetate was determined by running the fermenter at a range of different temperature points. The fermenter was initially run at 30° C., and the temperature was increased to a number of different temperatures. It was surprisingly found that the optimum temperature for fastest growth of bacteria was at least 32° C., or at least 33° C., or at least 34° C., or at least 35° C., or at least 36° C.

Yeast Fermentation Utilising Acids as a Substrate.

The invention has particular applicability to supporting the production of lipids from acetate containing substrates. One such type of substrate is acetate derived from the conversion of $H_2$ and $CO_2$ gases by anaerobic microbial fermentation.

Processes for the production of lipids from carbon sources such as glucose, xylose, lactose, glycerol and ethanol are known (Chi et al., "Oleaginous yeast *Cryptococcus curvatus* culture with dark fermentation hydrogen production effluent as feedstock for microbial lipid production" International Journal of Hydrogen Energy, Vol 36, 2011, pp 9542-9550.) Exemplary processes include those described for example by Chi et al.

A number of oleaginous yeasts are known to be capable of carrying out the fermentation of sugars to lipids, and are suitable for use in the process of the present invention. Examples of such yeasts that are suitable for use in the invention include those of the genus *Cryptococcus*, such as strains of *Cryptococcus curvatus* (also known as *Candida curvatus*) (Chi et al.)

*Cryptococcus curvatus* has been shown to produce lipids by fermentation of substrates comprising acetate. Chi et al. demonstrated the ability of *C. curvatus* to produce lipids in acetate fermentation.

Production of lipid(s) by fermentation of *C. curvatus* has been shown to be improved by a nitrogen limitation. A carbon to nitrogen ratio of 49:1 has been shown to have a significant impact on lipid production. *C. curvatus* is known to grow on a number of carbon sources including glucose, acetate and ethanol. The ideal pH for growth of *C. curvatus* is pH 7.

The ability of *C. curvatus* to grow on acetate and ethanol, make the product streams of the $CO_2/H_2$ fermentation process described herein, ideal fermentation substrates for the yeast fermentations. The product stream from the $CO_2/H_2$ fermentation is particularly ideal, as it is rich in acetate, and has a pH of around pH 7.

Other suitable yeasts include those of the genus, *Candida, Lipomyces, Rhodosporidium, Rhodotorula, Saccharomyces* and *Yarrowia*. In addition, it should be understood that other oleaginous yeasts may be applicable to the present invention as would be understood by a person of skill in the art. It will also be appreciated that the invention may be applied to a mixed culture of two or more yeasts.

It would be understood that other oleaginous bacteria or fungi including those from the group selected from Blakeslea, *Cryptococcus, Cunninghamella, Mortierella, Mucor, Phycomyces, Pythium, Thraustochytrium* and *Trichosporon* may also be applicable to the present invention.

Culturing of the yeast used in a method of the invention may be conducted using any number of processes known in the art for culturing and fermenting substrates using oleaginous yeasts.

Typically, fermentation is carried out in any suitable bioreactor, such as a continuous stirred tank reactor (CTSR), a bubble column reactor (BCR) or a trickle bed reactor (TBR). Also, in some embodiments of the invention, the bioreactor may comprise a first, growth reactor in which the microorganisms are cultured, and a second, fermentation reactor, to which fermentation broth from the growth reactor is fed and in which most of the fermentation product (lipids) is produced. The methods and systems of the invention are herein described with reference to the Figures.

Figure 1:
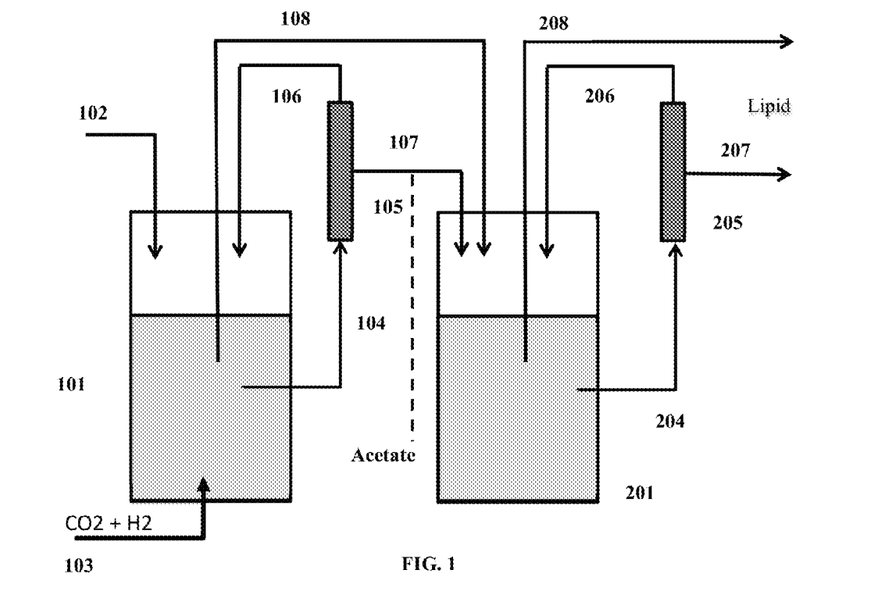
FIG. 1 is a two fermenter system for production of lipids from $CO_2$ and $H_2$ as defined by a second aspect of the present invention.
Figure 2:
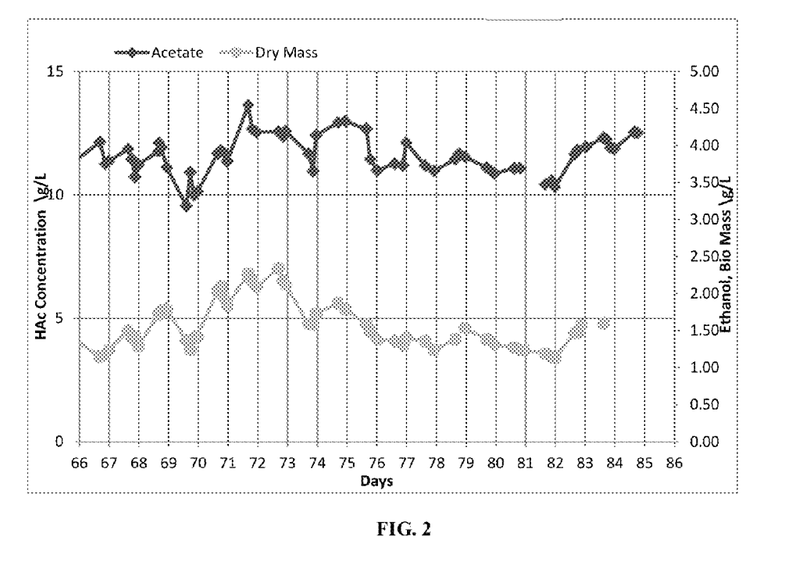
FIG. 2 shows acetate production from $CO_2$ and $H_2$ in accordance with one embodiment of the present invention.
Figure 3A:
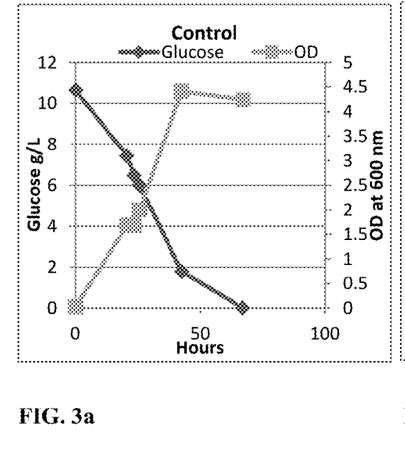
FIG. 3a shows growth of *C. curvatus* utilising a glucose substrate.
Figure 3B:
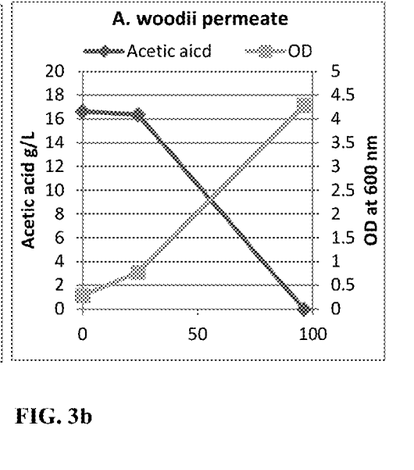
FIG. 3b shows growth of *C. curvatus* utilising an acetate substrate from a $CO_2/H_2$ fermentation process in accordance with the present invention.

FIG. 1 demonstrates a two stage system for the production of lipid(s) from a gaseous stream comprising $CO_2$ and $H_2$. The system provides a primary bioreactor 101 having a media inlet 102, a gas inlet port 103, a separator means 104, a permeate stream outlet 107, and a bleed stream outlet 108. The primary bioreactor is connected to a secondary bioreactor 201, having a separator 205, a permeate stream outlet 207 and a bleed stream outlet 208.

In use, the primary bioreactor 101 contains fermentation broth comprising a culture of one or more acetogenic bacteria in a liquid nutrient medium. Medium is added to the bioreactor 101 in a continuous or semi-continuous manner throughout the media inlet 102. A gaseous substrate is supplied to the bioreactor 101 via the gas inlet port 103. The separator means is adapted to receive at least a portion of broth from the bioreactor 101 via a first output conduit 104 and pass it through the separator 105 configured to substantially separate the microorganism cells (the retentate) from the rest of the fermentation broth (the permeate). At least a portion of the retentate is returned to the first bioreactor via a first return conduit 106 which ensures that the broth culture density is maintained at an optimal level. The separator 105 is adapted to pass at least a portion of the permeate out of the bioreactor 101 via a permeate delivery conduit 107. The permeate deliver conduit fees the cell free permeate to the secondary bioreactor 201. In certain embodiments of the invention, at least a portion of the cell free permeate is removed for product extraction or be recycled prior to the permeate stream being fed to the secondary bioreactor 201. A broth bleed output 108 is provided to directly feed broth from the primary bioreactor 101 to the secondary bioreactor 202. In certain embodiments the broth bleed and permeate bleed are combined prior to being fed to the secondary bioreactor. It may be desirable to purify the stream prior to passing to the secondary bioreactor to ensure a carbon:nitrogen ratio of at least 10:1 or at least 25:1 or at least 49:1.

The secondary bioreactor 202 contains a culture of one more oleaginous yeasts in a liquid nutrient medium. The secondary bioreactor receives broth and permeates from the primary bioreactor in a continuous or semi-continuous manner through broth bleed output 108 and permeate delivery conduit 107. The separator means is adapted to receive at least a portion of broth from the bioreactor 201 via a first output conduit 204 and pass it through the separator 205 configured to substantially separate the microorganism cells (the retentate) from the rest of the fermentation broth (the permeate). At least a portion of the retentate is returned to the first bioreactor via a first return conduit 206 which ensures that the broth culture density is maintained at an optimal level. The separator 205 is adapted to pass at least a portion of the permeate out of the bioreactor 201 via a permeate removal conduit 207. A broth bleed output 208 is provided to directly remove broth from the secondary bioreactor 201. The broth bleed stream is treated to remove the biomass for lipid extraction using known methods. The substantially biomass free bleed stream and the permeate streams are combined to produce a combines stream. In certain aspects of the invention, the combined stream can be returned to the primary reactor to supplement the liquid nutrient medium being continuously added. In certain embodiments it may be desirable to further process the recycle stream to remove an un-desired by products of the secondary fermentation. In certain embodiments, the pH of the recycle stream may be adjusted, and further vitamins and metals added to supplement the stream.

In certain embodiments, $CO_2$ produced as a by-product of the yeast fermentation process can be recycled to the primary bioreactor for use as a substrate. In preferred embodiments, that gas stream exiting the secondary bioreactor is treated to remove any trace oxygen prior to being passed to the primary bioreactor.

EXAMPLES

Example 1

Materials and Methods

Media:

Media at pH 6.5 was prepared as using the protocol defined by Balch et al (See, e.g., Balch et al, (1977) International Journal of Systemic Bacteriology, 27:355-361).

Bacteria: *Acetobacterium woodii* were obtained from the German Resource Centre for Biological Material (DSMZ). The accession number given to the bacteria is DSM 1030.

Fermentation in Bioreactor:

A three-liter reactor was filled with 1500 ml of the media. Oxygen was removed from the media by continuously sparging with $N_2$. The gas was switched from $N_2$ to a mixture of 60% $H_2$, 20% $CO_2$, and 20% $N_2$ 30 minutes before inoculation. The inoculum (150 ml) came from a continuous *Acetobacterium woodii* culture fed with the same gas mixture. The bioreactor was maintained at 30° C. and stirred at 200 rpm at the time of inoculation. During the following batch growth phase, agitation was increased incrementally to 600 rpm. The gas flow was increased incrementally by 50 ml/min according to the dropping $H_2/CO_2$ in the headspace as a result of the increasing biomass. To compensate for the acetic acid produced, the pH was automatically controlled to 7 using 5 M NaOH. Throughout the fermentation, a 0.5M solution of $Na_2S$ was pumped into the fermenter at a rate of 0.2 ml/hour. The culture was made continuous after 1 day. To reach high biomass along with high gas consumption, it is necessary to keep the acetate concentration in the fermenter at levels below 20 g/L. This was realized by running the fermenter at a relatively high dilution rate (D~1.7/day) while retaining the microbes in the fermenter with a polysulfon membrane filtration system with 0.1 µm pore size (GE healthcare hallow fibre membrane). The medium for the continuous culture was solution A excluding the composite trace metal solution, which was fed separately at a rate of 1.5 ml/hour using an automated syringe pump. The medium was degassed at least 1 day before and continuously degassing throughout fermentation process.

Sampling and Analytical Procedures:

Media samples were taken at intervals over a 30 day period

All samples were used to establish the absorbance at 600 nm (spectrophotometer) and the level of substrates and products (GC or HPLC). HPLC was routinely used to quantify the level of acetate.

Headspace of fermenter was analysed automatically by Gas-GC (Varian 4900 Micro-GC) at hourly.

Results

Over a thirty day period acetate is produced at a concentration of 12.5 g/L. The productivity rate of acetate averaged at 21.8 g/L per day.

The maximum concentration of acetic acid in a continuous culture was 17.76 g/L (296 mM)

Example 2

Methods and Materials

Bacteria: Oleaginous yeast *Cryptococcus curvatus* DSM 721 was revived in media containing glucose 10 g/L, yeast extract 1 g/L, and peptone 1 g/L.

1. The cultures were inoculated into permeate from an *Acetobacterium woodii* process. Cultures were fermented in a conical flask (50 ml of media in 250 ml flask) and at 25° C. and pH 7. *C. curvatus* grew in the permeate from the *A. woodii* process and converted all the acetic acid present in the permeate to biomass. The pH of culture increased from 7 to 9.3 in the culture.
2. A culture of *C. curvatus* was inoculated into permeate from the CO fermentation in a 2 L CSTR. B-vitamin and metals were added. Agitation was set at 300 rpm and the pH was adjusted to pH 6. During the run, the pH was adjusted to pH 7 and the culture showed the best growth at this pH as well as acetate consumption.
3. Lipid extraction: The *Cryptococcus curvatus* yeast was cultured in three different media, as follows; (i) medium comprising 10 g/L glucose; (ii) media comprising 15 g/L sodium acetate and (iii) permeate from a *A. woodii* fermentation process which contained 15 g/L acetate. Each media type was run in duplicate in flasks containing 250 ml of media. All flasks were incubated at 25° C. initially then the temperature was increased to 30° C.

Lipids were extracted from the biomass using known extraction methods. Given the size of the flasks, limited biomass was available for processing. Results were as follows: The Lipid concentration in the biomass of medium (i) contained 0.325%; lipid concentration in biomass of medium (ii) was 2.66%; and lipid concentration in medium (iii) was 4.88%.

The reference to any prior art in this specification is not, and should not be taken as, an acknowledgement or any form of suggestion that that prior art forms part of the common general knowledge in the field of endeavour in any country.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

What we claim is:

1. A method for producing lipids from a gaseous stream, the method comprising;
    a. flowing a substrate comprising C02 and H2 into a primary bioreactor comprising a culture of *Acetobacterium woodii*;
    b. anaerobically fermenting the substrate to produce a fermentation broth comprising at least one acid;
    c. flowing at least a portion of the fermentation broth to a secondary bioreactor comprising a culture of one or more oleaginous yeasts; and
    d. fermenting the at least one acid present in the fermentation broth to produce at least one lipid;
    wherein the one or more oleaginous yeast are selected from the group comprising *Candida, Lipomyces, Rhodosporidium, Rhodotorula, Saccharomyces, Yarrowia* and *Cryptococcus*.
2. The method of claim 1 wherein substantially all of the fermentation broth produced in the primary bioreactor is flowed to the secondary bioreactor.
3. The method of claim 1 wherein at least a portion of the at least one acid produced in the primary bioreactor is recovered.
4. The method of claim 1 wherein the acid is acetate.
5. The method of claim 1 further comprising;
    a. separating a broth stream exiting the secondary bioreactor to provide a biomass portion and a substantially biomass free waste stream;
    b. extracting one or more lipid products from the biomass portion; and
    c. passing at least a portion of the substantially biomass free waste stream to the primary reactor.

6. The method of claim 1 where the fermentation broth of the secondary bioreactor further comprises nitrogen and the ratio of acid to nitrogen is at least 10:1.

7. The method of claims 1 where the fermentation broth of the secondary bioreactor further comprises nitrogen and the ratio of carbon to nitrogen is at least 49:1.

8. The method of claim 4 wherein the acetate is produced at a concentration of at least 5 g/L.

9. The method of claim 8 wherein the acetate is produced at a concentration of at least 10 g/L.

10. The method of claim 4 wherein the acetate is produced at a rate of at least 40 g/L/day.

11. The method of claim 1 wherein the at least one yeast is *Cryptococcus curvatus*.

12. The method of claim 1 wherein the pH of both fermentations is from about pH 6 to about pH 8.

13. The method of claim 1 wherein the lipid is produced at a rate of at least 1 Og/L/day.

14. The method of claim 13 wherein the lipid is produced at a rate of at least 20 g/L/day.

15. The method of claim 1 further comprising a gas stream which exits the secondary bioreactor and is recycled to the primary bioreactor.

16. The method of claim 15 wherein the gas stream comprises $CO_2$.

17. The method of claim 16 wherein the gas stream is treated to remove trace amounts of oxygen prior to being passed to the primary bioreactor.

18. The method of claim 1 wherein the method is a continuous two stage fermentation process.

19. The method of claim 1 wherein at least a portion of the at least one lipid is recovered and converted to one or more tertiary products selected from the group consisting of biodiesel, ethanol and mixtures thereof.

20. The method of claim 1 wherein the substrate comprising $CO_2$ and $H_2$ is a gaseous substrate derived from an industrial process.

* * * * *